United States Patent [19]

Knuebel et al.

[11] Patent Number: 5,399,713
[45] Date of Patent: Mar. 21, 1995

[54] PROCESS FOR THE PRODUCTION OF 5,6-DIHYDROXYINDOLINES

[75] Inventors: Georg Knuebel, Duesseldorf; Guenther Konard, Hilden; Roswitha Michel, Duesseldorf, all of Germany

[73] Assignee: Henkel Kommanditgesellschaft auf Aktien, Duesseldorf, Germany

[21] Appl. No.: 199,283

[22] Filed: Mar. 18, 1994

[30] Foreign Application Priority Data

Sep. 2, 1991 [DE] Germany .............. 41 29 122.0

[51] Int. Cl.$^6$ .............................. C07D 209/08
[52] U.S. Cl. ............................. 548/490; 548/491
[58] Field of Search ........................ 548/490, 491

[56] References Cited

FOREIGN PATENT DOCUMENTS

| 0462857 | 12/1991 | European Pat. Off. | 548/490 |
| 2905054 | 8/1980 | Germany | 548/490 |
| 2908279 | 9/1980 | Germany | 548/490 |

OTHER PUBLICATIONS

CA116:158564K Hair Dyeing . . . Derivatives, Lagrange et al., p. 431, 1992.
Helv. Chim. Acta, 69(7), von Indu Parikh et al., pp. 1588–1596, 1986, (CAS Printout).
Helv. Chem. Acta 1968 (51) 1476–1494, von H. Wyler et al.
Journal of the Chemical Society (C) 1967, Letchworth GB pp. 1424–1427 S. N. Mishra et al. 'Studies related to the Chemistry of melanins. Part III. Synthesis of 5,6-dihydroxyindoline.' *p. 1425*.

*Primary Examiner*—Mary C. Lee
*Assistant Examiner*—Joseph K. McKane
*Attorney, Agent, or Firm*—Ernest C. Szoke; Wayne C. Jaeschke; Henry E. Millson, Jr.

[57] ABSTRACT

Process for the production of 5,6-dihydroxyindolines by ether cleavage of corresponding ether procursors with aqueous hydrogen bromide and subsequent direct crystallization from the aqueous reaction mixture.

18 Claims, No Drawings

PROCESS FOR THE PRODUCTION OF 5,6-DIHYDROXYINDOLINES

BACKGROUND OF THE INVENTION

1. Field of the Invention

This invention relates to a process for the production of 5,6-dihydroxyindolines by ether cleavage of corresponding ether precursors with hydrogen bromide and subsequent direct crystallization from the aqueous reaction mixture.

2. Statement of Related Art 5,6-Dihydroxyindoline, also known in the literature by the names of cyclodopamine and leuconorepinochrome, and 2-carboxy-5,6-dihydroxyindoline (synonyms: cyclodopa and leucodopachrome) are of considerable significance in the field of medicine and pharmacy and also hair dyes.

For example, natural hair dyes, so-called melanins, are formed in the course of their biosynthesis by oxidative polymerization of 5,6-dihydroxyindole. Accordingly, numerous attempts have been made in the past to use 5,6-dihydroxyindole as a reactive dye precursor in the dyeing of hair. Unfortunately, 5,6-dihydroxyindole is extremely unstable in aqueous solution both in its free form and in the form of its salts and, in the presence of atmospheric oxygen, rapidly forms insoluble, colored oxidation and polymerization products which themselves can no longer be fixed to the hair. Accordingly, attempts to use 5,6-dihydroxyindole itself or salts thereof in dye preparations involve considerable difficulties.

By contrast, it has been proposed to use 5,6-dihydroxyindolines as a pigment precursor in the biomimetic dyeing of hair. In this way, natural hair colors can be obtained with melanin dyes via a 5,6-dihydroxyindole formed in situ without having to accept any disadvantages due to the known stability problems of 5,6-dihydroxyindole.

The preparation of 5,6-dihydroxyindoline was described for the first time by S. N. Mishra and G. A. Swan (*J. Chem. Soc.* C 1967 1424). The authors obtained a solution of 5,6-dihydroxyindoline in hydrochloric acid by ether cleavage of 5,6-dimethoxyindoline in an autoclave at 150° C. The solution then had to be concentrated by evaporation and the resulting crude product purified from ether/ethanol. Unfortunately, this method is attended by several disadvantages: (1) the ether cleavage in an autoclave involves considerable effort with relatively large batches; (2) to recover the crude product, the reaction solution has to be completely concentrated by evaporation, so that considerable energy costs are incurred and the volume/time yield is reduced, and (3) the recrystallization from readily inflammable organic solvents represents a significant risk from the point of view of safety in use.

On the basis of the synthesis of 5,6-dihydroxyindoline by S. N. Mishra and G. A. Swan's method, M. Piatelli et al. developed an alternative synthesis pathway in which dopamine is first oxidized to norepichrome, the norepichrome is reduced to the leuco compound and the leuco compound is converted into triacetyl dihydroxyindoline. 5,6-Dihydroxyindoline is obtained in crude form from the triacetyl dihydroxyindoline after elimination of the acetyl groups. The purification corresponds to that described by S. N. Mischra and G. A. Swan. Apart from the complicated purification step, this method also has major disadvantages which prevent it from being applied on an industrial scale: (1) the oxidation step has to be carried out with a heavily diluted solution (approximately 0.5 g dopamine per liter) and (2) the intermediate triacetyl dihydroxyquinoline has to be purified by column chromatography.

In complete analogy to this method, the synthesis of 2-carboxy-5,6-dihydroxyindoline was described by H. Wyler and J. Choivini (*Helv. Chim. Acta* 1961 (51) 1476). They oxidized dopamethyl ester in the form of a highly dilute solution to form dopachrome methyl ester and reduced the dopachrome methyl ester in situ to form the leucodopachrome methyl ester which they then isolated as the triacetyl derivative. The triacetyl derivative was then subjected to acidic hydrolysis to form 2-carboxy-5,6-dihydroxyindoline (leucodopachrome). However, the method is attended by the disadvantages described above. Accordingly, the authors only obtained a few milligrams of product which was used for spectroscopic characterization.

According to EP-A-462 857, 5,6-dihydroxyindoline can be prepared by reaction of 5,6-dimethoxyindoline with aqueous HBr. After the reaction, the hydrobromic acid is distilled off, the residue is taken up in ethanol, treated with active carbon and filtered through Celite. Ethyl ether is then added to crystallize 5,6-dihydroxyindoline. This method is too complicated for industrial application.

DESCRIPTION OF THE INVENTION

Accordingly, there is a need for an improved process for the production of 5,6-dihydroxyindolines which, in particular, could even be carried out on a relatively large scale.

It has now surprisingly been found that 5,6-dihydroxyindolines can readily be obtained by reacting the corresponding ether precursors with hydrobromic acid and directly recrystallizing the 5,6-dihydroxyindolines from the aqueous reaction mixture.

Accordingly, the present invention relates to a process for the production of 5,6-dihydroxyindolines corresponding to general formula (I):

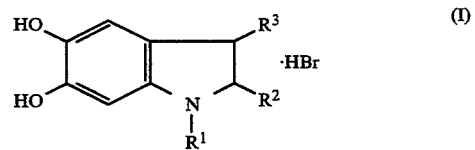

in which $R^1$ and $R^3$ independently of one another represent hydrogen or $C_{1-4}$ alkyl groups and $R^2$ is hydrogen, a $C_{1-4}$ alkyl group or a carboxyl group, by reaction of an indoline ether corresponding to general formula (II):

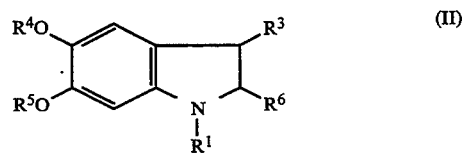

in which $R^1$ and $R^3$ independently of one another represent hydrogen or $C_{1-4}$ alkyl groups, $R^4$ and $R^5$ represent $C_{1-4}$ alkyl groups or, together with the oxygen atoms to which they are attached, form a $C_{1-4}$ alkylenedioxy group and $R^6$ is hydrogen, a $C_{1-4}$ alkyl group or a group $COOR^7$ or $CONR^7R^8$ and $R^7$ and $R^8$ are hydrogen or a $C_{1-4}$ alkyl group, with hydrobromic acid, the 5,6-dihydroxyindolines being directly crystallized out from the aqueous reaction mixture.

In one preferred embodiment of the invention, $R^3$ in formulae (I) and (II) is hydrogen. In another preferred embodiment, $R^1$ in formulae (I) and (II) is hydrogen or a methyl group, more particularly hydrogen.

Indoline ethers (II) in which $R^4$ and $R^5$ are $C_{1-4}$ alkyl groups are normally used in the process according to the invention. In the case of methyl groups, methyl bromide is formed therefrom in the course of the ether cleavage. Accordingly, it can be of advantage to use indoline ethers (II) in which $R^4$ and $R^5$ together with the oxygen atoms to which they are attached form a $C_{1-4}$ alkylenedioxy group, for example a methylenedioxy group or an isopropylidenedioxy group. The bromides formed during the ether cleavage in this case are less volatile and are preferred in the interests of greater safety in use.

The indoline ethers (II) used may be used either in free form or in the form of salts, for example the hydrochloride.

The process according to the invention may readily be carried out by heating the indoline ether (II) in an aqueous solution of hydrogen bromide. Basically, there is no particular limit to the concentration of the aqueous HBr, although 40 to 62% solutions are preferred. The molar ratio of hydrogen bromide to indoline ether (II) is adjusted to a value of 3:1 to 30:1 and preferably to a value of 5:1 to 15:1. The reaction mixture is then heated under reflux for several hours. The reaction mixture is worked up simply by cooling, the desired 5,6-dihydroxyindoline (I) crystallizing out. After filtration under suction and drying, the 5,6-dihydroxyindoline is obtained in highly pure form.

The 5,6-dihydroxyindolines obtained by the process according to the invention are suitable as a precursor for oxidation dyes of the type used in oxidation colorants for keratin fibers, particularly for human hair.

The following Examples are intended to illustrate the invention without limiting it in any way.

EXAMPLES Example 1

100 g of 5,6-dimethoxyindoline (0.6 mole) were introduced under nitrogen into a stirred vessel and 500 ml of a 62% aqueous hydrogen bromide solution (6.6 moles of HBr) were subsequently added. After careful heating, the reaction mixture was refluxed for 5 hours. After cooling to 60° C., the reaction mixture was filtered and 5,6-dihydroxyindoline was crystallized out overnight while cooling with ice. The product was filtered under suction and dried in vacuo.

Yield: 100 g of 5,6-dihydroxyindoline hydrobromide (0.46 mole; 78% of the theoretical) Melting point: 236°–238° C. (decomposition) Purity: 97.8% (according to HPLC)

Comparison Example 1

10 g of 5,6-dimethoxyindoline were introduced under nitrogen into a stirred vessel and 50 ml of concentrated HCl were added. After careful heating, the reaction mixture was refluxed for 5 hours. A thin-layer chromatogram of the reaction mixture did not show any 5,6-dimethoxyindoline or 5,6-dihydroxyindoline zones.

Comparison Example 2

10 g of 5,6-dimethoxyindoline were introduced under nitrogen into a stirred vessel and 50 ml of a 67% aqueous hydrogen iodide solution were added. After careful heating, the reaction mixture was refluxed for 5 hours. A thin-layer chromatogram of the reaction mixture did not show any 5,6-dimethoxyindoline or 5,6-dihydroxyindoline zones.

The Comparison Examples clearly show that 5,6-dihydroxyindoline can be satisfactorily prepared from 5,6-dimethoxyindoline solely with hydrobromic acid.

We claim:

1. A process for the production of a 5,6-dihydroxyindoline of formula (I)

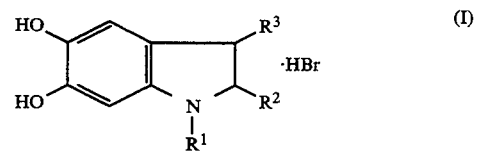

in which $R^1$ and $R^3$ independently of one another represent hydrogen or a $C_{1-4}$ alkyl group and $R^2$ is hydrogen, a $C_{1-4}$ alkyl group, or a carboxyl group, comprising the steps of A) reacting an idoline ether of formula (II) or a salt thereof

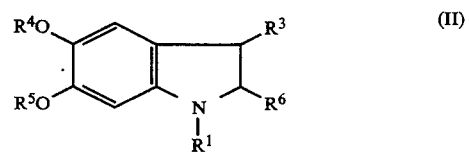

in which $R^1$ and $R^3$ independently of one another represent hydrogen or a $C_{1-4}$ alkyl group, $R^4$ and $R^5$ represent $C_{1-4}$ alkyl groups or, together with the oxygen atoms to which they are attached, form a $C_{1-4}$ alkylenedioxy group, and $R^6$ is hydrogen, a $C_{1-4}$ alkyl group or a group $COOR^7$ or $CONR^7R^8$ and $R^7$ and $R^8$ are hydrogen or a $C_{1-4}$ alkyl group, with an aqueous solution of hydrobromic acid;

B) cooling the resulting aqueous reaction mixture to crystallize the compound of formula I therefrom; and C) isolating the crystallized compound of formula I from the aqueous reaction mixture.

2. The process of claim 1 wherein in the indoline ether of formula II in step A, $R^3$ is hydrogen.

3. The process of claim 1 wherein in the indoline ether of formula II in step A, $R^1$ is hydrogen or a methyl group.

4. The process of claim 2 wherein in the indoline ether of formula II, $R^1$ is hydrogen or a methyl group.

5. The process of claim 4 wherein $R^1$ is hydrogen.

6. The process of claim 1 wherein in step A the indoline ether of formula II is in the form of the free amine.

7. The process of claim 1 wherein in the indoline ether of formula II in step A, $R^4$ and $R^5$ together with the oxygen atoms to which they are attached form a $C_{1-4}$ alkylenedioxy group.

8. The process of claim 1 wherein in step A the aqueous solution of hydrobromic acid contains from 40 to 62% hydrobromic acid.

9. The process of claim 1 wherein in step A the molar ratio of hydrobromic acid to the indoline ether of formula II is from 3:1 to 30:1.

10. The process of claim 9 wherein said molar ratio is from 5:1 to 15:1.

11. The process of claim 1 wherein in step A the reaction mixture is heated under reflux.

12. The process of claim 11 wherein the reaction mixture is heated under reflux for several hours.

13. The process of claim 1 wherein step C) is carried out by filtration under suction.

14. The process of claim 1 wherein in step A the molar ratio of hydrobromic acid to the indoline ether of formula II is from 3:1 to 30:1 and the reaction mixture is heated under reflux.

15. The process of claim 14 wherein in the indoline ether of formula II $R^1$ and $R^3$ are hydrogen.

16. The process of claim 14 wherein the indoline either of formula II is in the form of the free amine.

17. The process of claim 14 wherein said molar ratio is from 5:1 to 15:1.

18. The process of claim 14 wherein in the indoline ether of formula II, $R^4$ and $R^5$ together with the oxygen atoms to which they are attached form a $C_{1-4}$ alkylenedioxy group.

* * * * *